(12) United States Patent
Takeda et al.

(10) Patent No.: US 7,308,582 B2
(45) Date of Patent: Dec. 11, 2007

(54) COLLATION PROCESSING APPARATUS, DATA COMMUNICATION SYSTEM AND DATA COMMUNICATION METHOD

(75) Inventors: Toru Takeda, Saitama (JP); Tatsuo Itabashi, Tokyo (JP); Tomoshi Hirayama, Tokyo (JP)

(73) Assignee: Sony Corporation (JP)

( * ) Notice: Subject to any disclaimer, the term of this patent is extended or adjusted under 35 U.S.C. 154(b) by 831 days.

(21) Appl. No.: 10/398,518

(22) PCT Filed: Oct. 5, 2001

(86) PCT No.: PCT/JP01/08819

§ 371 (c)(1),
(2), (4) Date: Apr. 4, 2003

(87) PCT Pub. No.: WO02/29589

PCT Pub. Date: Apr. 11, 2002

(65) Prior Publication Data

US 2004/0044482 A1    Mar. 4, 2004

(30) Foreign Application Priority Data

Oct. 5, 2000    (JP)    ............... 2000-311738

(51) Int. Cl.
*H04L 9/00*    (2006.01)

(52) U.S. Cl. ............... 713/186; 713/168; 726/4; 726/27; 726/30

(58) Field of Classification Search ............... 702/19; 726/5, 4, 27, 30; 382/115; 713/168, 186
See application file for complete search history.

(56) References Cited

U.S. PATENT DOCUMENTS 6,016,476 A * 1/2000 Maes et al. ............... 705/1
6,047,268 A * 4/2000 Bartoli et al. ............... 705/35
6,765,470 B2 * 7/2004 Shinzaki ............... 340/5.52
6,823,454 B1 * 11/2004 Hind et al. ............... 713/168
6,910,131 B1 * 6/2005 Yamada et al. ............... 713/186

(Continued)

FOREIGN PATENT DOCUMENTS

JP    2-273861 A1    11/1990

(Continued)

OTHER PUBLICATIONS

Kazuo Takaragi et al., Firewall Internet Kanren Gijutsu ni tsuite, Jouhou Security Series, vol. 2, Shoukou-dou, Jun. 10, 1998, pp. 135-138.

*Primary Examiner*—Nasser Moazzami
*Assistant Examiner*—Shanto M Z Abedin
(74) *Attorney, Agent, or Firm*—Lerner, David, Littenberg, Krumholz & Mentlik, LLP

(57) ABSTRACT

A collation processing apparatus includes user identification information memory means for storing user identification information which identifies a user, collation information input means for inputting collation information, collating means for carrying out collation processing on the basis of the collation information input by the collation information input means, user identification information reading means for reading out predetermined user identification information from the user identification information memory means on the basis of a collation result by the collating means, and output means for outputting, to external equipment, user identification information which has been read out by the user identification information reading means, thereby making it possible to specify a user. By setting a communication address serving as user identification information in the external equipment by address setting means, data communication in which the user is specified can be carried out.

11 Claims, 9 Drawing Sheets

U.S. PATENT DOCUMENTS 6,957,338 B1 * 10/2005 Sumino ....................... 713/186
7,028,013 B2 * 4/2006 Saeki ............................ 705/64

FOREIGN PATENT DOCUMENTS

| | | |
|---|---|---|
| JP | 9-114891 A1 | 5/1997 |
| JP | 11-68988 A1 | 3/1999 |
| JP | 11-252068 A1 | 9/1999 |
| JP | 2000-123143 A1 | 4/2000 |
| JP | 2000-235528 A1 | 8/2000 |

* cited by examiner

COLLATION PROCESSING APPARATUS, DATA COMMUNICATION SYSTEM AND DATA COMMUNICATION METHOD

This invention relates to user certification, and more particularly to a collation processing apparatus, a data communication system and a data communication method for carrying out user certification in data communications on a network.

In recent years, users have been permitted to obtain, by data communication utilizing a communication network such as the internet, etc., various information from a server unit, etc. connected to the communication network. Users use computer devices represented by, e.g., personal computers (PC), etc. as terminal equipment which carry out such data communication.

Meanwhile, in computer devices as described above, identification information for identifying corresponding computer devices are set. On the network, the computer device is specified on the basis of such identification information so that transmission/reception of data is securely carried out.

Namely, a server unit which has received an information transmission request from a computer device through a network can identify this computer device on the basis of the identification information set at the computer device to transmit predetermined data to the computer device.

However, since this identification information is information for specifying a computer device which is carrying out data communication, but is not information for specifying a user who is using that computer device, the server unit would carry out delivery of information with respect to the computer device which has made the information transmission request irrespective of the identity of the user who is using the computer device.

SUMMARY OF THE INVENTION

An object of this invention is to provide a collation processing apparatus, a data communication system and a data communication method which are capable of specifying the user who is using a computer device to allow only that user to handle information relating to the user himself.

A collation processing apparatus according to the present invention is attached to an external equipment having a network connecting function, wherein the collation processing apparatus includes bio-information input means for inputting bio-information of a user; regular user bio-information memory means for storing regular user bio-information serving as bio-information of a regular user registered in advance; collating means for collating the bio-information input by the bio-information input means with the regular user bio-information stored in the regular user bio-information memory means; communication address memory means for storing a communication address serving as identification information which univocally determines the regular user on a network to which the external equipment is connected; communication address reading means for reading out the communication address of a collated regular user from the communication address memory means on the basis of a collation result by the collating means; communication address output means for outputting to the external equipment the communication address which has been read out by the reading means; and address setting means for setting the communication address output by the communication address output means in the external equipment.

This collation processing apparatus sets the communication address of the collated regular user in the external equipment.

A data communication system according to the present invention includes an information processing unit to which a collation processing unit is attached and a server unit connected through a network, wherein the collation processing unit comprises bio-information input means for inputting bio-information of a user, regular user bio-information memory means for storing regular user bio-information serving as bio-information of a regular user registered in advance, collating means for collating the bio-information input by the bio-information input means with the regular user bio-information stored in the regular user bio-information memory means, communication address memory means for storing a communication address serving as identification information which univocally determines the regular user on the network to which the information processing unit is connected, communication address reading means for reading out the communication address of a collated regular user from the communication address memory means on the basis of a collation result by the collating means, communication address output means for outputting to the information processing unit the communication address which has been read out by the communication address reading means, and address setting means for setting the communication address output by the communication address output means in the information processing unit, and wherein the information processing unit comprises input means for inputting the communication address output by the communication address output means of the collation processing unit, and communication means for carrying out data communication by using the communication address set by the address setting means of the collation processing unit.

In this data communication system, a communication address is acquired on the basis of the collation result at the collation processing unit, thereby making it possible to execute data communication for every user.

A data communication system according to the present invention includes an information processing unit to which a collation processing unit is attached and a server unit connected through a network, wherein the collation processing unit comprises bio-information input means for inputting bio-information of a user, regular user bio-information memory means for storing regular user bio-information serving as bio-information of a regular user registered in advance, collating means for collating bio-information input by the bio-information input means with regular user bio-information stored in the regular user bio-information memory means, user identification information memory means for storing user identification information which identifies the regular user, user identification information reading means for reading out predetermined user identification information from the user identification information memory means on the basis of a collation result by the collating means, user identification information output means for outputting to the information processing unit the user identification information which has been read out by the user identification information reading means, address acquiring means for acquiring a first communication address on the basis of the user identification information, electronic signature generating means for generating an electronic signature on the basis of the first communication address acquired at the address acquiring means, electronic signature attached address output means for outputting to the information processing unit the electronic signature generated at the electronic signature generating means in the state where the electronic signature is attached to the first communication address, second communication address receiving means for receiving a second communication address transmitted through the network and the information processing unit from the server unit, and address setting means for setting the second communication address received at the second communication address receiving means in the information processing unit, and wherein the information processing unit comprises user identification information input means for inputting the user identification information output by the user identification information output means of the collation processing unit, electronic signature attached address input means for inputting the first communication address and the electronic signature which have been output from the electronic signature attached address output means of the collation processing unit, and electronic signature attached address transmitting means for transmitting, through the network to the server unit, the first communication address and the electronic signature which have been input by the electronic signature attached address input means, and wherein the server unit comprises second communication address memory means for storing a second communication address, electronic signature attached address receiving means for receiving the first communication address and the electronic signature which have been transmitted through the network by the electronic signature attached address transmitting means of the information processing unit, certifying means for certifying the electronic signature attached to the first communication address received at the electronic signature attached address receiving means, reading means for reading out the second communication address from the second communication address memory means in accordance with the fact that the electronic signature has been certified by the electronic signature certifying means, and second communication address transmitting means for transmitting the second communication address which has been read out by the reading means to the collation processing unit attached to the information processing unit through the network.

In this data communication system, since user identification information is acquired on the basis of the collation result at the collation processing unit so that a user is specified, it is possible to execute data communication for every user.

A data communication method according to the present invention is provided for a data communication system in which an information processing unit to which a collation processing unit is attached and a server unit are connected through a network, the data communication method comprising allowing the collation processing unit to input bio-information of a user; allowing the collation processing unit to collate the input bio-information with regular user bio-information of a regular user registered in advance which is stored in regular user bio-information memory means; allowing the collation processing unit to read out a predetermined communication address on the basis of a collation result from a communication address serving as identification information which univocally determines, on the network, the regular user which is stored in communication address memory means; allowing the collation processing unit to output the communication address which has been read out to the information processing unit; allowing the collation processing unit to set the output communication address in the information processing unit; and allowing the information processing unit to carry out data communication by using the communication address which has been set by the collation processing unit.

In this data communication method, a communication address is acquired on the basis of a collation result at the collation processing unit, thereby making it possible to start data communication for every user.

A data communication method according to the present invention is provided for a data communication system in which an information processing unit to which a collation processing unit is attached and a server unit are connected through a network, the data communication method comprising allowing the collation processing unit to input bio-information of a user; allowing the collation processing unit to collate the input bio-information with regular user bio-information of a regular user registered in advance which is stored in regular user bio-information memory means; allowing the collation processing unit to read out user identification information which identifies the user which is stored in user identification information memory means; allowing the collation processing unit to output the user identification information which has been read out to the information processing unit; allowing the information processing unit to input the user identification information which has been output by the collation processing unit; allowing the collation processing unit to acquire a first communication address on the basis of the user identification information; allowing the collation processing unit to generate an electronic signature of the acquired first communication address; allowing the collation processing unit to output the generated electronic signature to the information processing unit in the state where the generated electronic signature is attached to the first communication address; allowing the information processing unit to input the first communication address and the electronic signature which have been output from the collation processing unit; allowing the information processing unit to transmit the first communication address and the electronic signature which have been input to the server unit though the network; allowing the server unit to receive the first communication address and the electronic signature which have been transmitted from the information processing unit through the network; allowing the server unit to certify the electronic signature attached to the received first communication address; allowing the server unit to read out a second communication address stored in second communication address memory means in accordance with the fact that the electronic signature has been certified; allowing the server unit to transmit the second communication address which has been read out to the collation processing unit attached to the information processing unit through the network; allowing the collation processing unit to receive the second communication address which has been transmitted through the network and the information processing unit from the server unit; and allowing the collation processing unit to set the received second communication address in the information processing unit.

In this data communication method, since user identification information is acquired on the basis of a collation result at the collation processing unit so that the user is specified, it is possible to start data communication for every user.

DETAILED DESCRIPTION

A collation processing apparatus, a data communication system and a data communication method according to this invention will be described below in detail with reference to the attached drawings.

Figure 1:
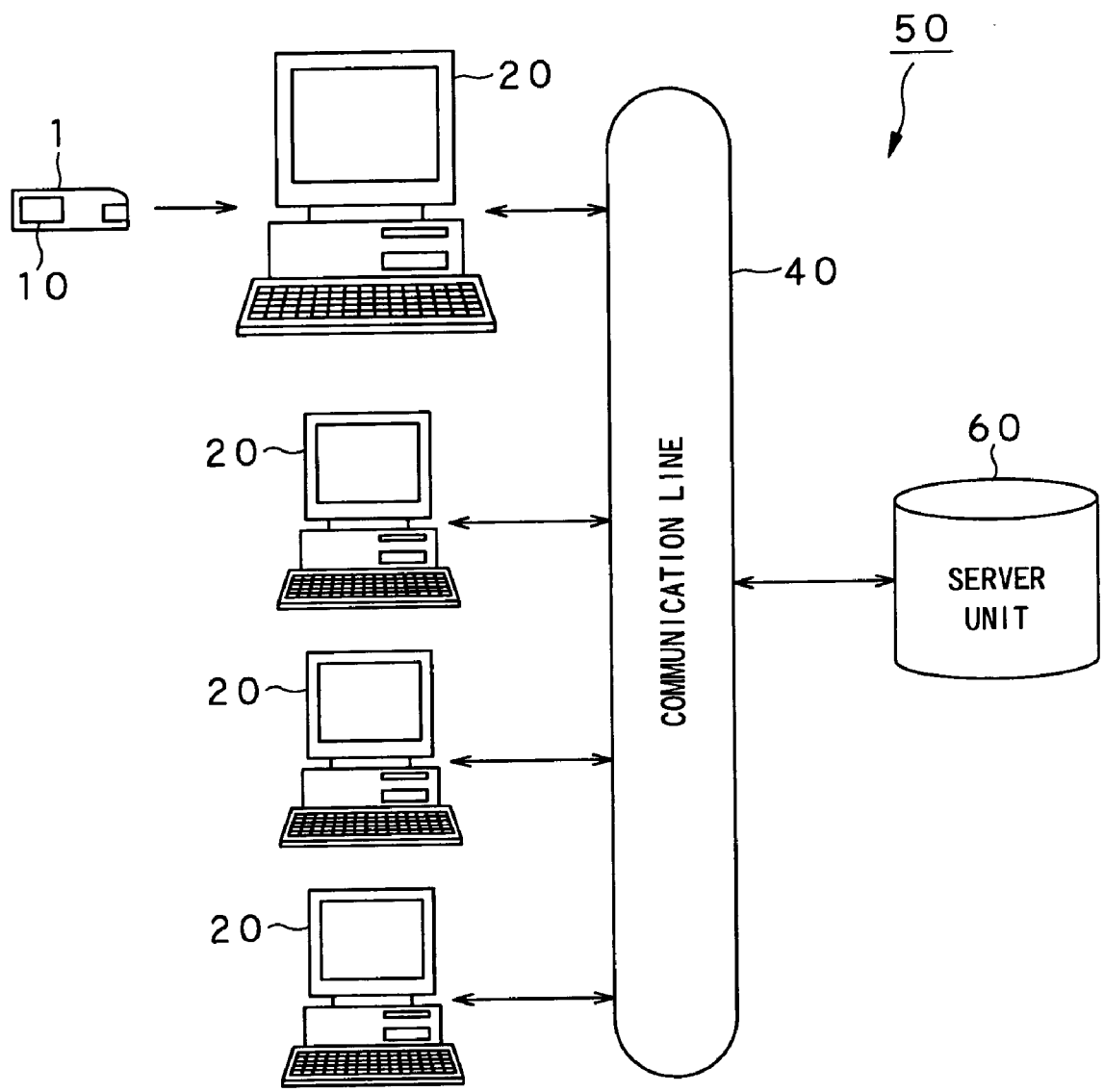
FIG. 1 is a view for explaining the configuration of a data communication system shown as a first embodiment of this invention.

This invention is applied to a data communication system 50 shown as a first embodiment in FIG. 1.

The data communication system 50 shown in FIG. 1 is adapted so that computer devices 20 and a server unit 60 are connected through a communication line 40, and the computer devices 20 function as the client of the server unit 60. In addition, the computer device 20 is adapted so that a memory card 1 which will be described in detail later can be attached, and can input data output from the attached memory card 1.

The memory card 1 is constituted as a recording medium including memory means and collating means, etc. and having an external appearance of a card shape removable with respect to the computer device 20, etc. As input means of collation information necessary for carrying out collation, there is provided a fingerprint reading portion 10 constituted by a semiconductor, etc. Namely, a user comes into contact with the fingerprint reading portion 10 to thereby carry out collation processing on the basis of a comparison with respect to a parameter registered in advance at the memory card 1. Further, in the case where it is determined as the result of collation that a corresponding user is the regular or proper user, it is possible to output certification information for permitting communication and user identification information, such as, for example, an address which can specify a user on the internet (a communication address such as an IP (Internet Protocol) address caused to have a one-to-one relationship with respect to an individual or a dynamic address for specifying an individual, etc.).

The computer device 20 is provided with an attachment/detachment mechanism (card slot) for the memory card 1, and can input certification information and user identification information output from the attached memory card 1. Moreover, the computer devices 20 are connected to the communication line 40, e.g., an analog public telephone line, public digital line such as ISDN (Integrated Service Digital Network), etc. or LAN (Local Area Network), etc., and are adapted to have the ability to carry out data communication through this communication line 40.

In this case, as a transmission path of the communication line 40, there may be employed wire, and there may be also used wireless, a communication satellite, etc. The communication line 40 may be in a form such as a LAN (Local Area Network), a WAN (Wide Area Network), etc. or a combination thereof.

The server unit 60 is connected to the communication line 40, and records predetermined data (contents), etc. into memory means (not shown). Further, in the case where a data transmission request is given from the computer device 20, etc. similarly connected to the communication line 40, the server unit 60 transmits requested data.

In the data communication system 50 shown as the first embodiment, certification information is delivered to the computer device 20 to which the memory card 1 has been attached, whereby data communication to and from the server unit 60 through the communication line 40 is started. Further, the server unit 60 carries out transmission of data on the basis of user identification information.

Namely, in the data communication system 50 shown in FIG. 1, the user who is using the computer device 20 is specified, and data communication is carried out.

It is to be noted that in the case where, e.g., the computer device 20 is connected in Peer-to-Peer form, there is no necessity to particularly store contents into memory means of the server unit 60.

The memory card 1 has an external appearance respectively illustrated as the front view, the plan view, the bottom view and the side view in FIGS. 2, 3, 4 and 5, wherein the casing is formed of molded plastic.

Figure 2:
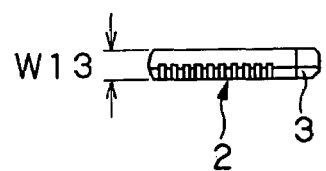
FIG. 2 is a front view for explaining the external appearance of a memory card.
Figure 4:
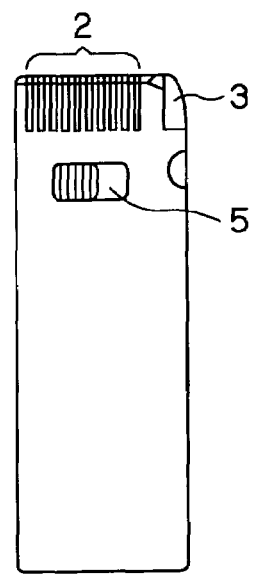
FIG. 4 is a bottom view for explaining the external appearance of the memory card.
Figure 5:
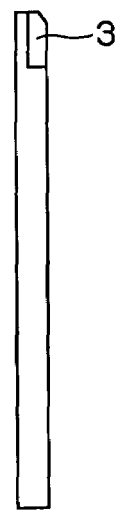
FIG. 5 is a side view for explaining the external appearance of the memory card.

The memory card 1 is adapted so that a terminal portion 2 having, e.g., ten (10) electrodes is formed from the front lower portion toward the bottom surface side of the casing as shown in the front view of FIG. 2 and the bottom view of FIG. 4. At this terminal portion 2, as information input/output means, the output of certification information and user identification information and/or the input, etc. of various parameters for collation, etc. are carried out.

It is to be noted that while the information input/output means employs the configuration of the contact type having electrodes as the terminal portion 2 as described above, there may be employed a configuration for carrying out data communication by non-contact.

Figure 3:
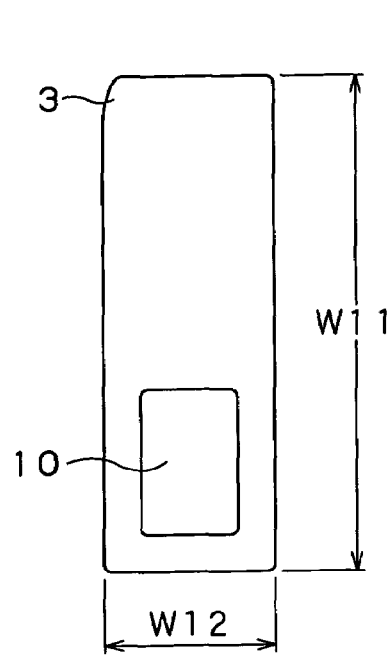
FIG. 3 is a plan view for explaining the external appearance of the memory card.

As shown in the plan view of FIG. 3, at the left upper portion when viewed from the plan face side of the casing, a cut portion 3 is formed. This cut portion 3 serves to prevent an error in the insertion direction when this memory card 1 is fitted or attached into the card slot of the computer device 20, etc.

Moreover, as shown in the plan view of FIG. 3, at the plane face side of this memory card 1, the fingerprint reading portion 10 is formed. The fingerprint reading portion 10 is formed at the other end side of the terminal portion 2 in the length direction of the memory card 1. When the memory card 1 is attached with respect to the computer device 20, the end portion of this memory card 1 where the fingerprint reading portion 10 is formed is exposed from the computer device 20.

Further, as shown in the bottom view of FIG. 4, at the bottom surface side, a slide switch 5 for preventing erroneous erasing of data which has been recorded into this memory card 1 is formed.

Moreover, as a practical size of the memory card 1, e.g., widths W11, W12, W13 shown in FIGS. 2 and 3 are respectively represented by W11=50 mm, W12=21.5 mm, W13=2.8 mm.

Figure 6:
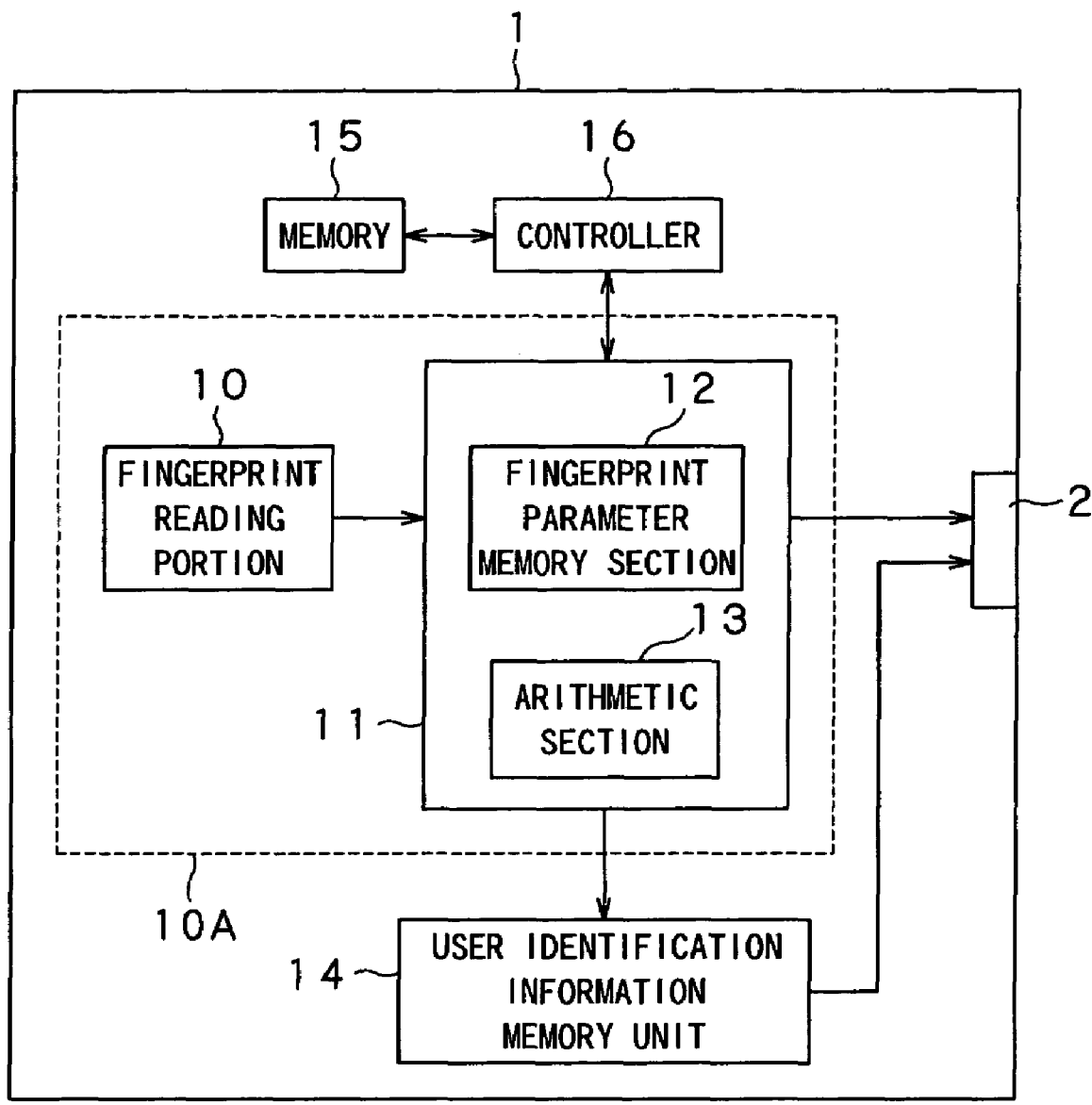
FIG. 6 is a block diagram for explaining the internal configuration of the memory card in the data communication system shown as the first embodiment.

Subsequently, the outline of the configuration of the memory card 1 will be explained by using the block diagram shown in FIG. 6. The memory card 1 comprises the above-described terminal portion 2, the fingerprint reading portion 10, a collating unit 11, a user identification information memory unit 14, a memory 15 and a controller 16.

The fingerprint reading portion 10 is adapted to automatically scan a fingerprint as the result of the fact that the finger of a user comes into contact therewith, thus making it possible to read the fingerprint by, e.g., electrostatic capacity, etc. A fingerprint which has been read at the fingerprint reading portion 10 is delivered to the collating unit 11 as an input fingerprint parameter.

The collating unit 11 comprises a fingerprint parameter memory section 12 and an arithmetic section 13. At the fingerprint parameter memory section 12, fingerprint information of a user is stored as a parameter. The fingerprint information of the user is used as reference information when collation is carried out. Moreover, the arithmetic section 13 carries out comparative collation between the input fingerprint parameter from the fingerprint reading portion 10 and the stored fingerprint parameter stored in the fingerprint parameter memory section 12, whereby in the case where it is determined that both parameters are in correspondence with each other, the arithmetic section 13 sends out certification information to the controller 16 as a collation result.

The user identification information memory unit 14 stores user identification information which can specify a user on the network. The user identification information is a network address, etc. Further, where it is determined at the collating unit 11 that both parameters are in correspondence with each other so that certification information is sent to the controller 16, corresponding user identification information is read out by the controller 16.

The user identification information which has been read out by the controller 16 is output to the computer device 20 through the terminal portion 2.

The memory 15 is adapted so that various programs are stored in the case where processing is executed in the memory card 1.

The controller 16 executes various processing on the basis of the programs stored in the memory 15, and controls respective functional portions of this memory card 1 in a generalized manner.

In this example, the memory 15 serving as a storage section provided at the memory card 1 is a non-volatile semiconductor memory element or a volatile semiconductor memory element. In the case where a volatile semiconductor memory element is used, a power supply is required for the purpose of storing and holding information stored in the element. For this reason, a battery for supplying power is provided.

Furthermore, the above-described fingerprint reading portion 10 and the collating unit 11 will also be called a fingerprint certification processing unit 10A in the following description because an operation to mainly conduct fingerprint collation to carry out certification is made.

Moreover, since certification processing of a user is executed, it is the premise that the memory card 1 is a SAM (Secure Access Module) having a tamper tolerance such that data caused to undergo transmission/reception between the collating unit 11 and the controller 16 is not stolen, or data stored in the fingerprint parameter memory section 12 or the user identification information memory unit 14 is not read out externally or is not illegally or unfairly tampered with.

In addition, the fingerprint scanning method at the fingerprint reading portion 10, the data format of the detected input fingerprint parameter, the storage method for the stored fingerprint parameter, the method of comparison between the input fingerprint parameter and the stored fingerprint parameter, and the criterion for the comparative judgment are not particularly limited, and various technologies can be utilized.

Figure 7:
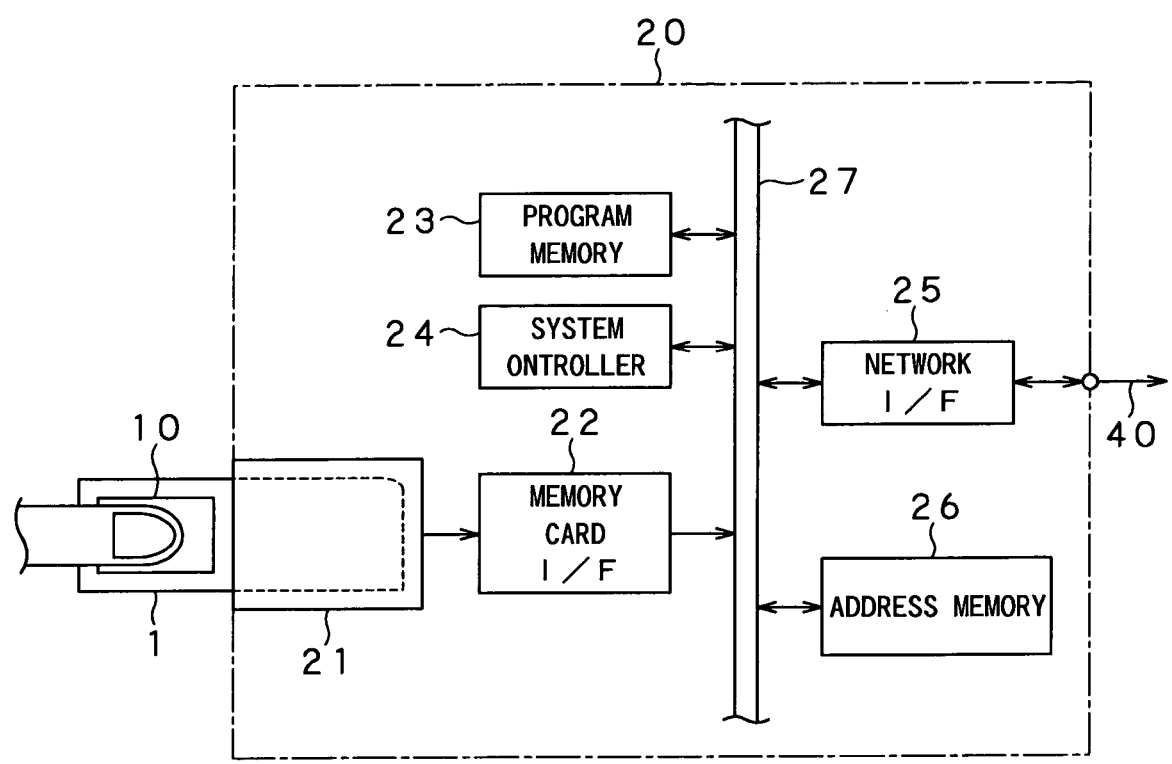
FIG. 7 is a block diagram for explaining the internal configuration of a computer device.

An outline of the configuration of the computer device 20 will now be described by using the block diagram shown in FIG. 7.

The computer device 20 comprises a memory slot 21, a memory card I/F (interface) 22, a program memory 23, a system controller 24, a network I/F (interface) 25, and an address memory 26.

The memory slot 21 is an attachment/detachment mechanism for the memory card 1 (card slot), and is an interface for loading the memory card 1 with respect to this computer device 20.

This memory slot 21 is formed so that the fingerprint reading portion 10 can be faced to the outside of the casing of this computer device 20 as described above in the state where the memory card 1 is attached.

Moreover, the memory slot 21 is provided with a terminal portion of the contact type. When this terminal portion and the terminal portion 2 of the above-described memory card 1 are connected, the input/output of data can be carried out between the memory card 1 and the computer device 20.

Further, in the case where data communication is carried out with the terminal portion 2 serving as a terminal portion of the non-contact type, data communication means of the non-contact type corresponding thereto is also provided at the memory slot 21.

The memory card I/F 22 is an interface when the computer device 20 carries out data communication to and from the memory card 1.

The program memory 23 stores various programs executed at the computer device 20.

The system controller 24 reads out various programs stored in the program memory 23 as occasion demands to execute them. In addition, the system controller 24 controls respective functional portions of this computer device 20 in a generalized manner.

The network I/F 25 is an interface in the case where data communication is carried out through the communication line 40 to which the server unit 60 is connected in a manner explained by using FIG. 1.

Figure 8:
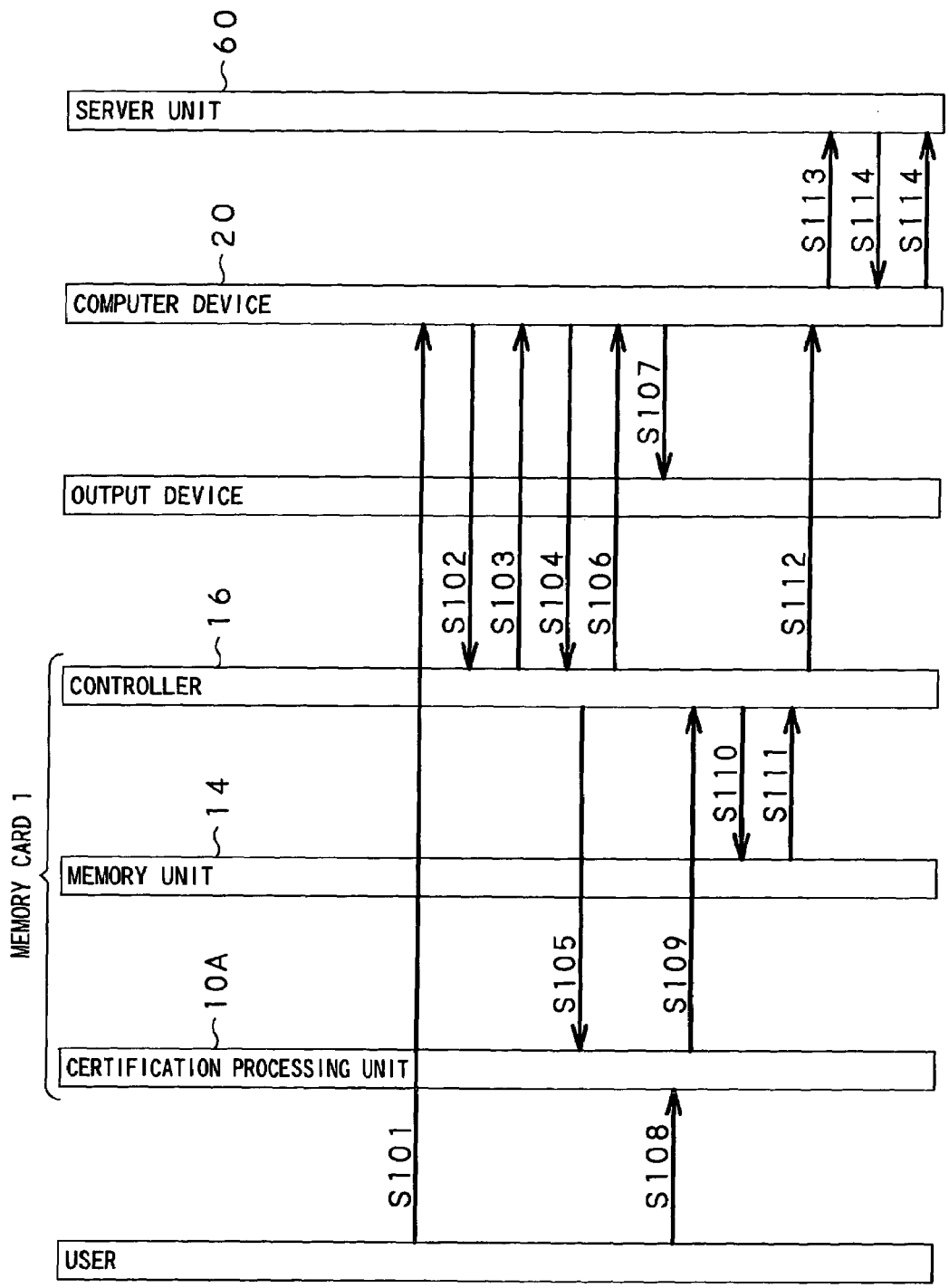
FIG. 8 is a timing chart for explaining the operation of the data communication system shown as the first embodiment.

An explanation will be given below by using the timing chart shown in FIG. 8 in connection with an operation in which data communication is started in the data communication system 50.

First, at step S101, a user operates a power ON switch (not shown) of the computer device 20 to place the computer device 20 in the ON state to start it.

At step S102, simultaneously with the fact that the computer device 20 is placed in the ON state, the system controller 24 and peripheral modules are initialized. The initialized system controller 24 starts communication to the controller 16 of the memory card 1 via a bus and the memory card I/F 22 in order to confirm that a suitable memory card 1 is attached at the memory slot 21 of this computer device 20.

At step S103, since energization of the computer device 20 already results in a communicatable state, the controller 16 of the memory card 1 transmits an Acknowledge command including the own device type information with respect to a communication request from the computer device 20 (ACK:Acknowledge).

At step S104, when the system controller 24 of the computer device 20 confirms a device type of the memory card 1, it starts certification processing corresponding to the device type. The system controller 24 transmits a certification request command to the controller 16 of the memory card 1. When the certification request command is transmitted to the controller 16, the following processing results in processing within the memory card 1.

At step S105, the controller 16 first outputs an initialization command to the fingerprint certification processing unit 10A in order to execute fingerprint certification processing.

The fingerprint certification processing unit 10A is a functional unit for executing fingerprint certification, which is composed of the fingerprint reading portion 10 and the collating unit 11 of the memory card 1 as described above, and serves to detect the fingerprint of the user at the fingerprint reading portion 10 to execute certification of the fingerprint detected at the collating unit 11.

At step S106, the controller 16 transmits a message notifying that initialization has been completed to the system controller 24 of the computer device 20.

At step S107, the system controller 24 of the computer device 20 hastens the user to carry out fingerprint certification by using an output device connected to the computer device 20 in response to the fact that the initialization completion notification has been received.

For example, in the case where the output device is a display device, this display device is caused to display a message such as "Please touch finger". In the case where the output device is an audio output device, a beep sound is given to thereby hasten the user to carry out fingerprint certification. In addition, when the display device is caused to display user guidance in which the method of fingerprint certification is indicated in detail, even a user who first utilizes this system can easily carry out fingerprint certification.

At step S108, when the user places his finger on the fingerprint reading portion 10 of the fingerprint certification processing unit 10A, the fingerprint reading portion 10 automatically scans the finger to acquire fingerprint data to allow it to be input as a fingerprint parameter. The input fingerprint parameter is compared and collated with a stored fingerprint parameter at the collating unit 11 of the fingerprint certification processing unit 10A. Thus, conformity or nonconformity is determined.

At step S109, the fingerprint certification processing unit 10A of the memory card 1 outputs a fingerprint collation result to the controller 16.

At step S110, when the controller 16 receives the fingerprint collation result that the input fingerprint parameter and the stored fingerprint parameter are in conformity with each other, the controller 16 certifies that the user who has been caused to undergo fingerprint collation is a proper user to make the address information acquisition request to the user identification information memory unit 14.

Moreover, when the controller 16 receives the fingerprint collation result that the input fingerprint parameter and the stored fingerprint parameter are not in conformity with each other, fingerprint collation transmits a message indicating certification failure to the system controller 24 of the computer device 20 to complete certification processing. In this case, the computer device 20 disables (functionally stops) the network function so that only stand alone utilization can be made.

At step S111, the user identification information memory unit 14 outputs address information of a corresponding user to the controller 16 in accordance with an address information acquisition request.

At step S112, when the controller 16 acquires address information, it transmits the acquired address information to the computer device 20 as a response to the certification request command which has been transmitted from the system controller 24 of the computer device 20 at step S104.

At step S113, the system controller 24 of the computer device 20 starts communication to and from the server unit 60 by utilizing the address acquired from the memory card 1.

At step S114, communication is being carried out between the computer device 20 and the server unit 60.

Since the user can be identified by the memory card 1 in the data communication system 50 shown as the first embodiment as stated above, when there is used a computer device 20 in which this memory card 1 is attached so that data communication can be carried out on the basis of certification information, even if any computer device 20 is selected, it becomes possible to provide access to a network formed by the communication line 40 as the computer device peculiar to the user.

Moreover, since the user is specified by a fingerprint, even if another user uses memory card 1, it is impossible to obtain certification information. Accordingly, there is also no possibility that the memory card 1 may be abused.

With respect to data caused to actually undergo communication, there are mentioned, e.g., transmission/reception of electronic mail or pay contents such as music data for pay delivery, etc. Since data can be transmitted after the specifying of the user has been carried out in the above-described data communication system 50, it is possible to securely and safely execute data transmission.

Additionally, as the valid term of the certification information, there is employed a time period during which the memory card 1 is attached, etc. Namely, there is employed a scheme such that certification information is reset at the time point when data communication is completed and the memory card 1 is detached from the computer device 20.

Moreover, the server unit 60 may be provided with a charging processing section which carries out charging processing (not shown). Since the charging processing section executes a charging operation as the result of the fact that the user is certified and is specified, this server unit 60 can carry out charging processing for every user. Thus, also at the user side, it is possible to exclude improper charging resulting from the fact that the terminal equipment has been unfairly used by a third person.

Figure 9:
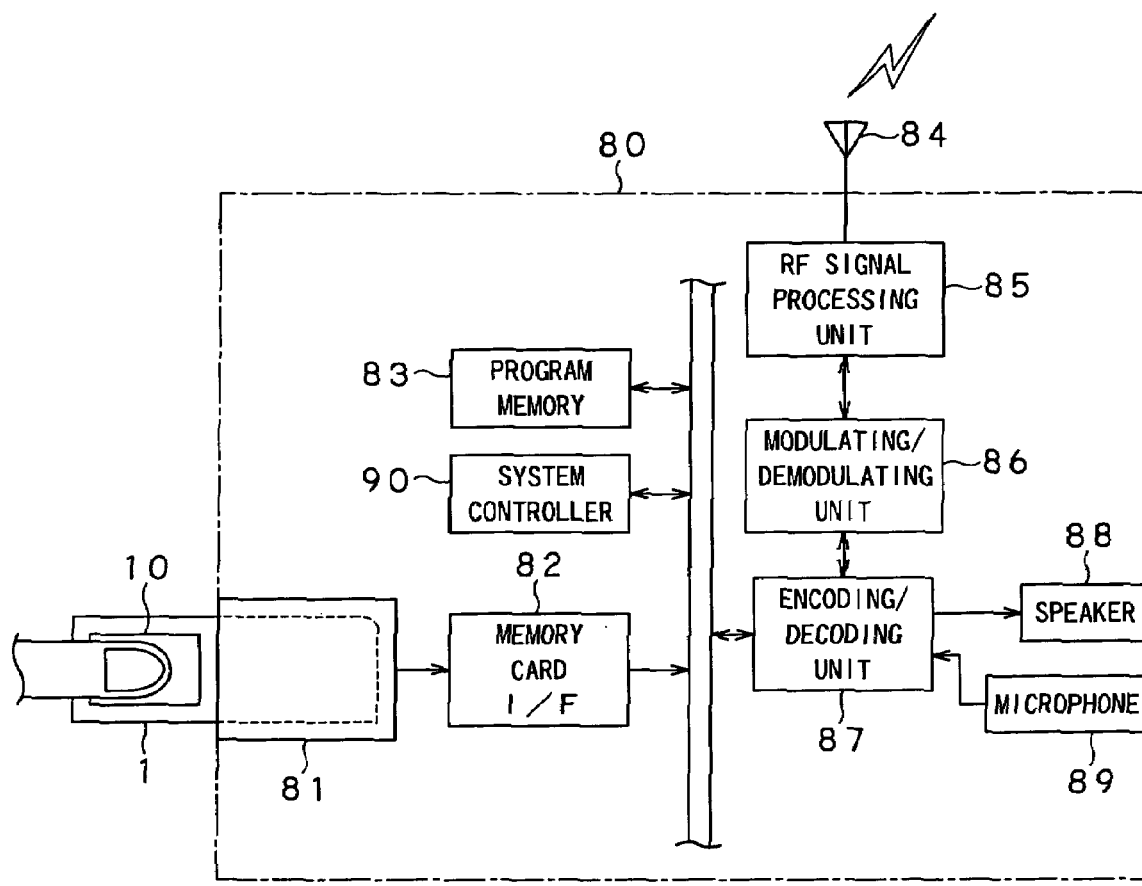
FIG. 9 is a block diagram for explaining the internal configuration of a mobile phone.

While there is disclosed in the above-described explanation the data communication system 50 which carries out data communication by using the computer device 20 as the terminal equipment that the user uses, a mobile phone 80 as shown in FIG. 9 may also be used in place of the computer device 20.

As shown in FIG. 9, the mobile phone 80 comprises a memory slot 81 adapted so that memory card 1 can be attached, a memory card I/F 82, a program memory 83, an antenna 84, an RF (Radio Frequency) signal processing unit 85, a modulating/demodulating unit 86, an encoding/decoding unit 87, a speaker 88, and a microphone 89.

The memory slot 81 is an attachment/detachment mechanism for the memory card 1 (card slot), and an interface for attaching the memory card 1 with respect to the mobile phone 80.

The memory slot 81 is formed so that the fingerprint reading portion 10 can be faced to the outside of the casing of the mobile phone 80 in the state where the memory card 1 is attached.

Moreover, the memory slot 81 is provided with a terminal portion of the contact type in this embodiment. When this terminal portion is connected to the terminal portion 2 of the above-described memory card 1, input/output of data can be carried out between the memory card 1 and the mobile phone 80.

Further, in the case where data communication is carried out with the terminal portion 2 serving as a terminal portion of the non-contact type, data communication means of the non-contact type corresponding thereto is also provided at the memory slot 81.

The memory card I/F 82 is an interface when the mobile phone 80 carries out data communication to and from the memory card 1.

The program memory 83 stores various programs executed at the mobile phone 80.

The antenna 84 receives call signals or audio signals, etc. from a base station (not shown) to deliver such signals to the RF signal processing unit 85 to transmit audio signals delivered from the RF signal processing unit 85 to the base station (not shown).

The RF signal processing unit 85 amplifies an output of radio frequency, and/or carries out control relating to radio frequency.

The modulating/demodulating unit 86 carries out demodulation processing of an audio signal delivered from the RF signal processing unit 85 to deliver the audio signal thus processed to the encoding/decoding unit 87 to carry out modulation processing of audio data encoded at the encoding/decoding unit to deliver the audio data thus processed to the RF signal processing unit 85.

The encoding/decoding unit 87 decodes an audio signal delivered from the modulating/demodulating unit 86 to deliver the audio signal thus decoded to the speaker 88 to encode the audio signal delivered from the microphone 89 so that audio data is provided to deliver the audio data to the modulating/demodulating unit 86.

The speaker 88 is an output interface for outputting a voice during a telephone conversation, operation sound of the mobile phone 80, or receiving notification sound for notifying the user that a radio wave has been received, etc.

The microphone 89 is an input interface for inputting a voice during a telephone conversation.

A system controller 90 reads out various programs stored in the program memory 83 as occasion demands to execute them. In addition, the system controller 90 controls respective functional portions of the mobile phone 80 in a generalized manner.

The receiving path will be described. A signal (e.g., audio signal) received at the antenna 84 is delivered to the modulating/demodulating unit 86 through the RF signal processing unit 85. Further, at the modulating/demodulating unit 86, a predetermined demodulation process is carried out. The signal thus processed is decoded at the encoding/decoding unit 87, and is delivered to the speaker 88.

In addition, the transmitting path will be described. A voice input from the microphone 89 is encoded as audio data by the encoding/decoding unit 87. Further, at the modulating/demodulating unit 86, a predetermined modulation processing is carried out. Further, the audio data which has been caused to undergo modulation processing is transmitted from the antenna 84 through the RF signal processing unit 85.

The mobile phone 80 receives a general calling signal which has designated user identification information from a base station (not shown) at the antenna 84, whereby in the case where user identification information corresponding to the mobile phone 80 is detected at the encoding/decoding unit 87 through the RF signal processing unit 85 and the modulating/demodulating unit 86, audio data of received packets is decoded to deliver the decoded audio data to the speaker 88. Namely, the mobile phone 80 is adapted so that even if a packet is received in which other user identification information is indicated, this device ignores such packet. Accordingly, a telephone conversation is continued as if the mobile phone 80 is usually connected.

By constituting the mobile phone 80 in this way, the user is not required to select a specific telephone device. For example, in the case where there is employed a kind of device in which a slot is provided for insertion of memory card 1, even if the telephone device is a mobile phone of another person or a wire-type telephone device, it is possible to realize charging with respect to the user's own telephone device and a receiving operation with respect to the user's own telephone device. For this reason, such mobile phone can be used. Accordingly, since it is impossible to obtain certification information by the memory card 1 even if the user's own mobile phone 80 is lent to another person, or mobile phone 80 is stolen, it becomes possible to eliminate the possibility that the mobile phone 80 may be illegally or unfairly used.

The network communication and/or telephone conversation by the telephone device can be carried out in this way, whereby facilities are improved as compared to the case where identification information are assigned to terminal equipment themselves, and illegal or unfair use can be prevented in advance.

A data communication system 150 shown in FIG. 10 as a second embodiment of this invention will now be described.

Meanwhile, in the case where certification is carried out by the collation of the fingerprint in the above-described data communication system 50 shown as the first embodiment, there is employed such an approach to send user identification information by a combination of the memory card 1 in which user identification information is stored and the person concerned who has carried out the collation of the fingerprint by the fingerprint reading portion 10. However, when a third person who has carried out "steal-reading" at any portion of the network executes "impersonation", there is the possibility that such impersonation cannot be excluded.

In view of the above, in the data communication system 150 shown as the second embodiment of this invention, there is employed a configuration to add a mutual certification processing function with respect to a network to thereby exclude an "impersonating" action.

Figure 10:
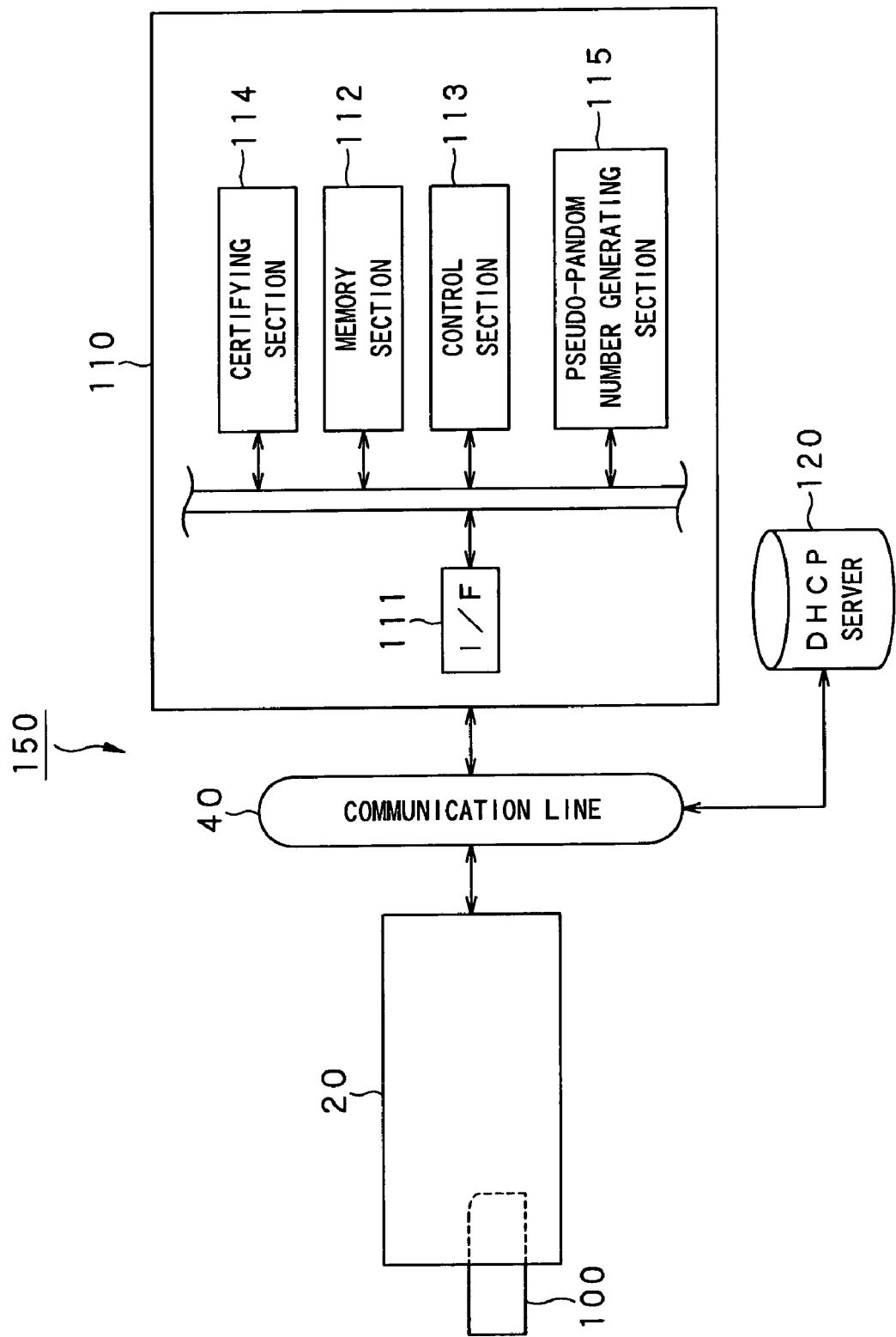
FIG. 10 is a view for explaining the configuration of a data communication system and the internal configuration of a server unit shown as a second embodiment of this invention.
Figure 11:
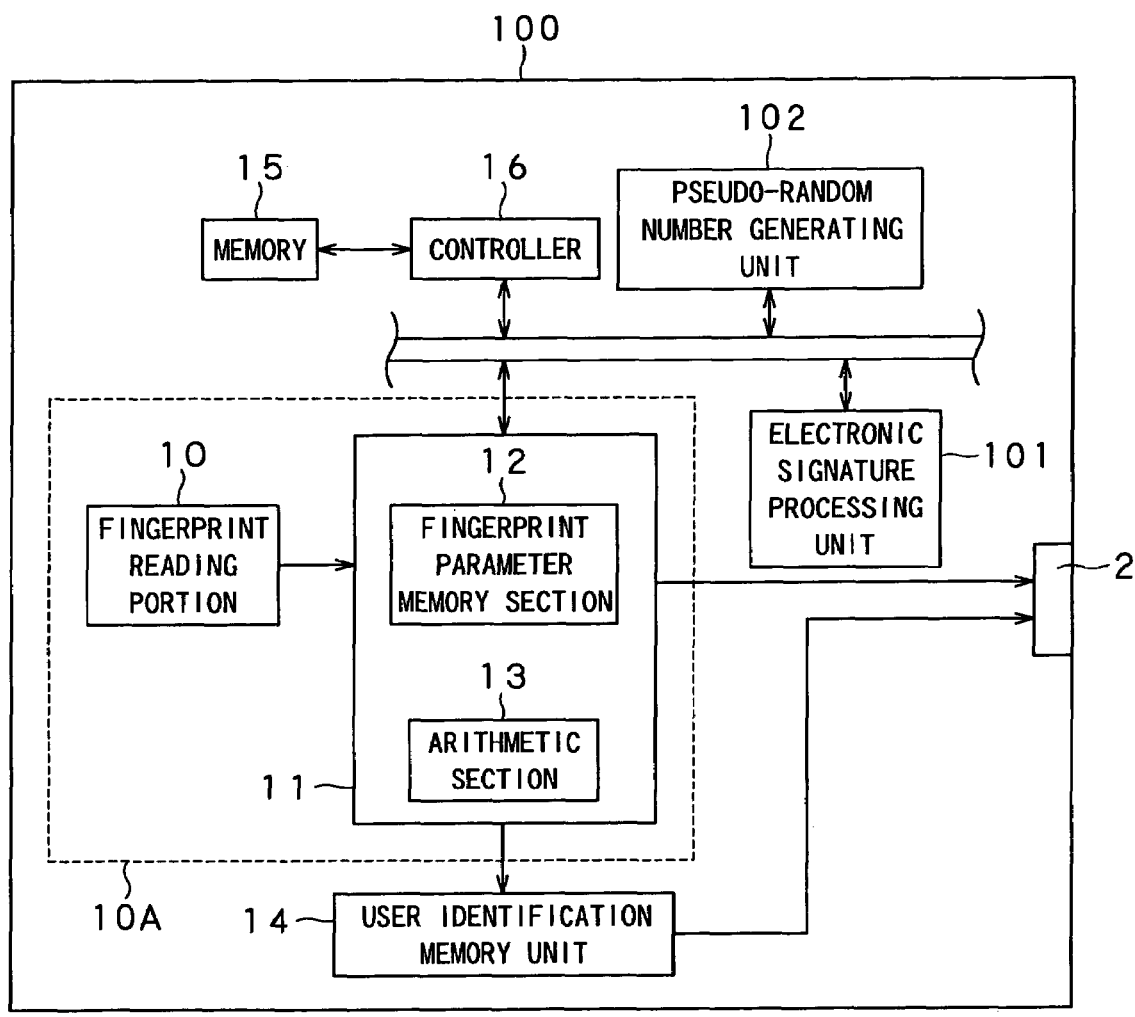
FIG. 11 is a block diagram for explaining the internal configuration of a memory card in the data communication system shown as the second embodiment.

First, in the data communication system 150, a memory card 100 as shown in FIG. 11 is used in place of the memory card 1, and a server unit 110 has the configuration shown in FIG. 10.

Initially, the configuration of the server unit 110 will be described by using FIG. 10.

The server unit 110 comprises a network I/F 111 which is an interface for connecting a communication line 40 and the server unit 110, a memory section 112 for storing and holding the network address of the user, a control section 113, a certifying section 114, and a pseudo-random number generating section 115.

The memory section 112 is adapted so that the network address of the terminal equipment, e.g., computer device 20, etc. connected to the server unit 110 through the communication line 40 is stored therein. When it is certified that a corresponding communication opposite party is a proper communication opposite party, the network address stored in the memory section 112 is read out by the certifying section 114, and is transmitted to the communication opposite party.

In addition, the memory section 112 stores a secret key used for an electronic signature given at the server unit 110, and holds an open key for decoding the electronic signature given to information transmitted from the communication opposite party, e.g., computer device 20. These keys are timely read out as occasion demands, and are used.

It is to be noted that in the case where a desired open key does not exist at the memory section 112, the desired open key may be acquired from the network by using a directory access protocol such as X.509 (ITU-T recommendation: International Telecommunication Union-Telecommunication Standardization Sector) or LDAP (Lightweight Directory Access Protocol). In addition, in place of obtaining an open key by the directory access, it is also possible to acquire the desired open key from open keys recorded on a removable recording media.

The control section 113 decodes an electronic signature given to information transmitted from the communication opposite party, e.g., computer device 20, by using a corresponding open key to carry out certification of the electronic signature. When certification of the electronic signature is carried out, the control section 113 sends out a registration request to the certifying section 114.

The certifying section 114 carries out processing for certifying a communication destination of the server unit 110. The certifying section 114 transmits random-generated information generated at pseudo-random number generating section 115 which will be described later in the state where an electronic signature generated by using a secret key of the server unit 110 is given in order to certify that the corresponding communication opposite party is a proper communication opposite party, e.g., computer device 20. In addition, the certifying section 114 certifies the communicating transmission opposite party in accordance with the fact that information that the server unit 110 itself has transmitted is sent back in the state where the electronic signature of the communication opposite party is given.

Further, the certifying section 114 reads out, from the memory section 112, a new network address used for future communication to give an electronic signature thereto to transmit it to the computer device 20.

On the other hand, the certifying section 114 gives an electronic signature generated by using the secret key of the server unit 110 to the information transmitted in the state where the electronic signature is given in order to allow the communication opposite party, e.g., computer device 20, to certify whether or not this server unit 110 is a proper communication opposite party to send back such information.

The pseudo-random number generating section 115 generates information consisting of numeric values arranged at random which is transmitted in order to certify whether or not a communication destination which carries out communication with the server unit 110 through the communication line 40 is a proper communication opposite party. As information generated here, it is not required that the information itself has meaningful content. The information generated at the pseudo-random number generating section 115 is transmitted to the certifying section 114, and is transmitted to the communication destination in the state where the electronic signature is given.

It is to be noted that the memory section 112, the control section 113, the certifying section 114 and the pseudo-number generating section 115 provided in the server unit 110 may be respectively provided with network connection interfaces, and may be respectively independently connected to the communication line 40.

Subsequently, the memory card 100 will be described by using FIG. 11.

At the memory card 100, an electronic signature processing unit 101 and a pseudo-random number generating unit 102 are added to the memory card 1 used in the data communication system 50 shown as the first embodiment. Accordingly, an explanation of the functional portions overlapping with the functional portions of the memory card 1 will be omitted.

The electronic signature processing unit 101 executes processing based on PKI (Public key Infrastructure). The electronic signature processing unit 101 implements an electronic signature to information transmitted from the memory card 100, and/or implements encipherment processing thereto. The electronic signature processing unit 101 can execute both the symmetrical encipherment system using a common cipher key and the asymmetrical encipherment system using a cipher key and an open key.

The electronic signature processing unit 101 holds secret keys used in carrying out electronic signature for every user registered in advance.

Moreover, the electronic signature processing unit 101 holds an open key corresponding to the secret key of the communication opposite party registered in advance, e.g., server unit 110. Thus, the electronic signature processing unit 110 certifies the electronic signature of the server unit 110.

Further, the electronic signature processing unit 101 enciphers the information and the electronic signature by using the open key of the server unit 110 in order to prevent information from being stolen through the communication line 40 or tampered with or altered, except that the electronic signature processing unit 101 carries out an electronic signature with respect to information transmitted to the communication opposite party, e.g., server unit 110.

Here, the electronic signature will be described.

Generally, the electronic signature is also called Digital Signature, and is generated by enciphering information by using a secret key that only a person who transmits information knows.

The electronic signature is used in place of the certification seal in the paperless system using electronic mail, etc.

A receiving person who has received a telegram in which an electronic signature is given can decode the electronic signature by using an open decode key. When a telegram with an electronic signature transmitted from a transmitting person is decoded by this open decode key so that the name of the transmitting person and/or date appear, it is verified that this telegram is a telegram from a transmitting person who has the secret key.

Namely, in the electronic signature (digital signature), a function in which encipherment can be carried out only by limited persons and a decoding operation can be carried out by any recipient is realized.

In order to generate an electronic signature in a more practical sense, information in which an electronic signature is desired to be given is first input to a hash function to obtain a hash value. By enciphering the hash value thus obtained by a secret key that the user himself has and an open algorithm which is an encipherment algorithm, an electronic signature is obtained. The electronic signature is transmitted to the communication opposite party along with the information which is an ordinary sentence.

The communication opposite party who has received information in which an electronic signature is given carries out certification of the electronic signature. In order to certify the electronic signature, the received information which is an ordinary sentence is first input to a hash function to obtain a hash value. On the other hand, the electronic signature transmitted along with the information is decoded by an open algorithm and an open key corresponding to the secret key. When the decoded electronic signature is the same as the hash value, the electronic signature transmitted along with the information is certified. Thus, it is possible to determine that the information has been transmitted from a proper opposite party.

The pseudo-random number generating unit 102 generates information used when terminal equipment to which the memory card 100 is attached, e.g., computer device 20, certifies its communication opposite party. The pseudo-random number generating unit 102 can prevent the information transmitted at the time of certification processing from being the same every time because it generates information consisting of random numeric values.

The certification processing using random information generated at the pseudo-random number generating unit 102 is executed in place of certification processing using an electronic signature generated at the electronic signature processing unit 101, or in addition to certification processing using an electronic signature generated at the electronic signature processing unit 101, and it is possible to use both processing in the certification processing.

Moreover, as shown in FIG. 10, in the data communication system 150 shown in the second embodiment, a unit having a function to dynamically address for session via a network from a remote place like a DHCP (Dynamic Host Configuration Protocol) server 120 may be connected to the communication line 40 here on the network.

The DHCP server 120 is a server which holds plural network addresses, and can dynamically give a held network address in accordance with a request of terminal equipment connected on the network. The computer device 20 can acquire a network address from the DHCP server 120 in addition to acquiring a network address from the user identification information memory unit 14 of the memory card 100. In this case, the network address that the computer device 20 acquires from the DHCP server 120 is not a formal network address, but a network address temporarily used when mutual certification between the computer device 20 and the server unit 110 which will be described in detail later is carried out.

Since it is not limited that network addresses that the DHCP server 120 gives to the terminal equipment, i.e., the computer device 20 in this example, are the same every time, wiretapping by a third party can be reduced.

Figure 12:
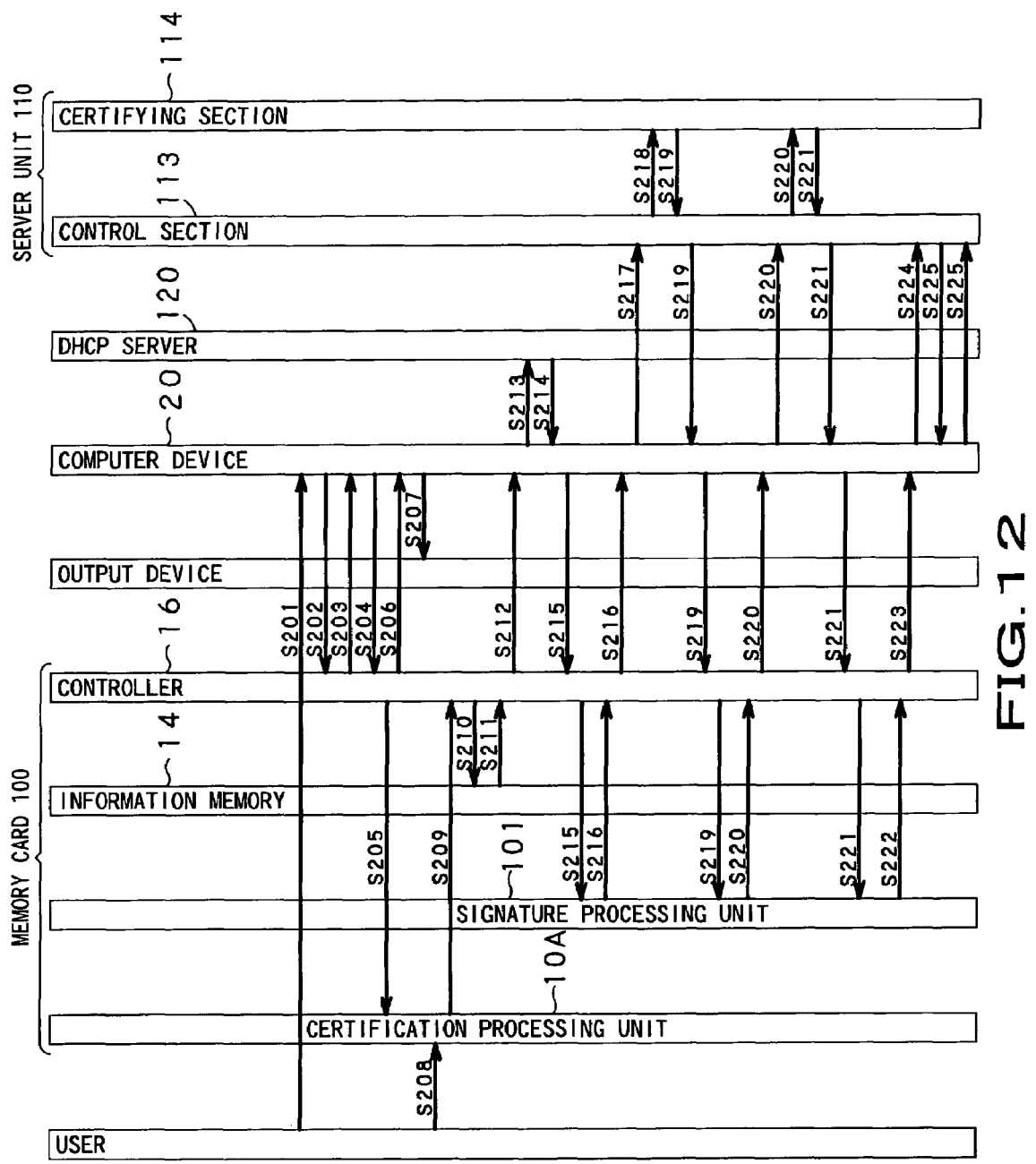
FIG. 12 is a timing chart for explaining the operation of the data communication system shown as the second embodiment.

The operation when data communication is started in the data communication system 150 shown as the second embodiment will now be described by using the timing chart shown in FIG. 12.

At step S201, the computer device 20 is placed in an ON state to start the computer device 20. In this example, it is assumed that the computer device 20 is turned ON by attaching the memory card 100 into the memory slot 21 of the computer device 20.

At step S202, the system controller 24 of the computer device 20 and peripheral modules are initialized simultaneously with energization. The initialized system controller 24 starts communication to and from the controller 16 of the memory card 100 via a bus and the memory card I/F 22 in order to confirm that a suitable memory card 100 is attached into the memory slot 21 of the computer device 20.

At step S203, since the controller 16 of the memory card 100 is already placed in a communicatable state by energization with respect to the computer device 20, it transmits an Acknowledge command including own device type information with respect to a communication request from the computer device 20 (ACK:acknowledge).

At step S204, when the system controller 24 of the computer device 20 confirms the device type of the memory card 100, it starts certification processing corresponding to the device type. The system controller 24 transmits a certification request command to the controller 16 of the memory card 100.

At step S205, the controller 16 first outputs an initialization command to the fingerprint certification processing unit 10A in order to execute fingerprint certification processing.

The fingerprint certification processing unit 10A is composed of a fingerprint reading portion 10 and a collating unit 11 of the memory card 100, and serves to detect the fingerprint of the user at the fingerprint reading portion 10 to execute certification of the fingerprint detected at the collating unit 11.

At step S206, the controller 16 transmits a message which notifies completion of initialization to the system controller 24 of the computer device 20.

At step S207, the system controller 24 of the computer device 20 hastens the user to carry out fingerprint certification by using an output device connected to the computer device 20 in accordance with the fact that the system controller 24 has received the initialization completion notification.

For example, in the case where the output device is a display device, the display device is caused to display a message like "Please touch finger". In the case where the output device is an audio output device, a beep sound is given to hasten the user to carry out fingerprint certification. In addition, the display device is caused to display user guidance in which the method of fingerprint certification is indicated in detail, whereby even a user who first utilizes this system can easily carry out fingerprint certification.

At step S208, when the user puts his finger on the fingerprint reading portion 10 of the fingerprint certification processing unit 10A, the fingerprint reading portion 10 automatically scans the finger to acquire fingerprint data to allow it to be input as a fingerprint parameter. The input fingerprint parameter is compared and collated with a stored fingerprint parameter at the collating unit 11 of the fingerprint certification processing unit 10A. Thus, conformity or nonconformity is determined.

At step S209, the fingerprint certification processing unit 10A of the memory card 100 outputs a fingerprint collation result to the controller 16.

At step S210, when the controller 16 receives the fingerprint collation result that the input fingerprint parameter and the stored fingerprint parameter are in conformity with each other, it recognizes that the user who has carried out fingerprint collation is a proper user to request the user identification information memory unit 14 to output ID (IDentification) data of a certified user.

At step S211, the user identification information memory unit 14 outputs ID data of the user in accordance with the ID data output request from the controller 16.

At step S212, the controller 16 outputs the ID data which has been output from the user identification information memory unit 14 to the system controller 24 of the computer device 20.

At step S213, the system controller 24 transmits an address acquisition request to the DHCP (Dynamic Host Configuration Protocol) server 120 connected to the communication line 40 in order to acquire the address that this computer device 20 temporarily uses in the certification processing with respect to the server unit 110. In this case, the address subject to the acquisition request is called an address ID in the following description because it is temporarily used for certification, and the address used in data communication after mutual certification is called a network address. Thus, a distinction is made therebetween.

It is to be noted that there may be employed an approach to skip processing at this step S213 to acquire the network address from the user identification information memory unit 14 that this memory card 100 has like the data communication system 50 shown in the first embodiment.

At step S214, the DHCP server 120 connected to the communication line 40 dynamically assigns an address ID to the computer device 20 in accordance with an address ID acquisition request of the system controller 24 of the computer device 20.

At step S215, the system controller 24 of the computer device 20 issues an electronic signature giving request to the controller 16 of the memory card 100 so as to give an electronic signature to the address ID assigned from the DHCP server 120 at the electronic signature processing unit 101.

At step S216, the electronic signature processing unit 101 gives an electronic signature (hereinafter the address ID and the electronic signature assigned from the DHCP server 120 will also be called address information) by control of the controller 16.

The electronic signature processing unit 101 inputs the address ID to a hash function to obtain a hash value of fixed length. Further, the electronic signature processing unit 101 enciphers the address ID and the hash value by using a predetermined open algorithm and a secret key corresponding to the acquired address ID that the electronic signature processing unit 101 holds to thereby generate an electronic signature.

Moreover, the electronic signature processing unit 101 may encipher address information by the open key of the server unit 110. This is a process for preventing wiretapping or tampering in carrying out the transmitting operation from the computer device 20 to the server unit 110 at a step which will be described later.

The address information is output from the electronic signature processing unit 101 to the controller 16. Further, the controller 16 outputs the address information to the system controller 24 of the computer device 20 to thereby respond to the electronic signature request of step S215.

At step S217, the system controller 24 of the computer device 20 transmits the address information and the ID data acquired at step S212 to the control section 113 of the server unit 110 through the network I/F 25.

At step S218, the control section 113 inputs, to the hash function, the address ID which is an ordinary sentence of the address information in accordance with the fact that the control section 113 has received the address information and the ID data to obtain a hash value. Further, the control section 113 decodes the electronic signature by using the electronic signature, a predetermined open algorithm and an open key corresponding to transmitted ID data that the control section 113 holds to certify the electronic signature when the same value as the hash value is obtained.

At this time, in the case where encipherment is carried out by an open key of the server unit 110 at step S216, a decoding operation is first carried out by using the own secret key thereafter to execute certification of the electronic signature.

When certification of the electronic signature is completed, the control section 113 sends out a registration request to the certifying section 114.

At step S219, the certifying section 114 transmits, to the electronic signature processing unit 101, information X generated at random at the pseudo-random number generating section 115, information in which an electronic signature is given to the information X, address information transmitted from the computer device 20 and information in which an electronic signature is given to the address information in accordance with a registration request which has been sent out from the control section 113.

The information X generated at random at the pseudo-random number generating section 115 is information that the server unit 110 uses in order to certify whether or not the computer device 20 connected to the communication line 40 is a proper communication opposite party.

The information transmitted from the certifying section 114 to the electronic signature processing section 101 is output from the certifying section 114, and is then transmitted to the electronic signature processing unit 101 through the control section 113 of the server unit 110, the computer device 20 and the controller 16 of the memory card 100.

At step S220, the electronic signature processing unit 101 of the memory card 100 certifies the server unit 110 communicating via the network in accordance with the fact that output address information has been sent back from the server unit 110 of the transmitting opposite party in the state where the electronic signature has been given at step S216.

Further, the electronic signature processing unit 101 sends the information X transmitted from the certifying section 114 of the server unit 110 back to the certifying section 114 in the state where the electronic signature is given.

In this instance, information X and the electronic signature transmitted from the electronic signature processing unit 101 to the certifying section 114 are output from the electronic signature processing unit 101, and are then transmitted to the certifying section 114 through the controller 16, the computer device 20 and the control section 113 of the server unit 110.

At step S221, the certifying section 114 of the server unit 110 certifies communicating computer device 20 via the network in accordance with the fact that the information X that the server unit 110 itself transmits is sent back in the state where the electronic signature of the computer device 20 is given.

Further, the certifying section 114 reads out a new network address used for future communication from the memory section 112 to transmit the network address to the computer device 20 in the state where the electronic signature is given.

In this instance, the network address which is to be transmitted is output from the certifying section 114, and is then transmitted to the electronic signature processing unit

101 through the control section 113 of the server unit 110, the computer device 20 and the controller 16 of the memory card 100.

At step S222, the electronic signature processing unit 101 confirms by the given electronic signature whether or not the transmitted network address is a correct address.

When the electronic signature processing unit 101 certifies that the transmitted network address is a correct network address, it outputs the certified network address to the controller 16.

At step S223, the controller 16 outputs the output network address to the system controller 24 of the computer device 20.

At step S224, the system controller 24 of the computer device 20 starts communication to and from the server unit 110 by making use of the network address transmitted from the memory card 100.

At step S225, communication is being carried out between the computer device 20 and the server unit 110. As described above, in the data communication system 150 shown as the second embodiment, when the computer device 20 and the server unit 110 which are connected to the communication line 40 carry out data communication, mutual certification is first carried out by using an electronic signature to give the address for data communication from the server unit 110 to the computer device 20. Thus, data communication is started.

By carrying out mutual certification in conducting data communication in a manner stated above, it is possible to prevent "impersonation" by a third party.

In addition, the server unit 110 may be provided with a charging processing section for carrying out charging processing (not shown). Since the charging processing section executes charging with respect to a user ID acquired from the user identification information memory unit 14 because the user has been certified, the server unit 110 can carry out charging processing for every user.

Thus, also at the user side, it is possible to exclude unreasonable charging based on the fact that the terminal equipment has been unfairly used by a third party. The charging processing at the charging processing section is started resulting from the fact that mutual certification is carried out so that the network address is transmitted from the server unit 110.

It is to be noted that although examples in which the fingerprint reading portion 10 is provided as input/output means in the memory card have been mentioned in the first and second embodiments, there may be employed, as input means, voice input means, image pick-up means, rainbow-colored pattern collating means, and eyeground retina pattern means, etc.

In the collation processing apparatus according to the present invention, a communication address is acquired on the basis of collation processing by collating means, thereby making it possible to univocally specify a user on the network. For this reason, it becomes possible to set a communication address obtained at the external equipment to which the collation processing unit (apparatus) is attached to execute data communication of high security through the network.

Moreover, since collation of bio-information, read-out of a communication address and the setting thereof can be executed by the collation processing apparatus, if only the collation processing apparatus is possessed, the collation processing apparatus is attached only to an information processing unit to which such collation processing apparatus can be attached, thereby making it possible to carry out data communication through the network. For this reason, usability by a user is improved, and it becomes possible to effectively utilize the existing external equipment connectable to the network.

Further, the electronic signature generating means is provided, thereby making it possible to prevent unfair or illegal access based on "impersonation" by a third party.

In the data communication system according to the present invention, a communication address is acquired on the basis of collation processing by the collating means of the collation processing apparatus, thereby making it possible to univocally specify a user on the network. For this reason, an acquired communication address is set at an information processing unit to which the collation processing apparatus is attached to have the ability to execute data communication of high security through the network.

Moreover, since collation of bio-information, read-out of a communication address and the setting thereof can be executed by the collation processing apparatus, if only the collation processing apparatus is possessed, the collation processing apparatus is attached to an information processing unit to which the collation processing apparatus can be attached, thereby making it possible to carry out data communication through the network. For this reason, usability by the user is improved, and it becomes possible to effectively utilize the existing information processing unit connectable to the network.

In the data communication system according to the present invention, user identification information is acquired on the basis of collation processing by the collating means of the collation processing apparatus to further acquire a second data communication address from the server unit, thereby making it possible to univocally specify a user on the network. For this reason, the acquired second communication address is set in the information processing unit to which the collation processing apparatus is attached to have the ability to execute data communication of high security through the network.

Further, since collation of bio-information, read-out of a communication address and the setting thereof can be executed by the collation processing apparatus, if only the collation processing apparatus is possessed, the collation processing apparatus is attached only to an information processing unit to which such collation processing apparatus can be attached, thereby making it possible to carry out data communication through the network. For this reason, usability by the user is improved, and it becomes possible to effectively utilize the existing information processing unit connectable to the network.

Further, since charging can be carried out by the charging means for every user in place of units of terminal equipment at the server unit, improper charging processing can be excluded.

Furthermore, mutual certification between the collation processing apparatus and the server unit is executed by the first certification processing means provided at the collation processing apparatus and the second certification processing means provided at the server unit thereafter to give a second communication address to the information processing apparatus, thereby making it possible to prevent unfair or illegal access based on "impersonation" by a third party.

In the data communication method according to the present invention, a communication address is acquired on the basis of collation processing by the collation processing apparatus, thereby making it possible to univocally specify a user on the network. For this reason, it is possible to execute data communication of high security to and from an information processing unit connected through the network.

In the data communication method according to the present invention, user identification information is acquired on the basis of collation processing by the collation processing apparatus to further acquire a second data communication address from the server unit, thereby making it possible to univocally specify a user on the network. For this reason, the acquired second communication address is set in the information processing unit to which the collation processing apparatus is attached to have the ability to execute data communication of high security through the network.

Further, since charging can be carried out for every user in place of units of terminal equipment by charging means at the server unit, it is possible to exclude improper or illegal charging operations.

In addition, mutual certification between the collation processing apparatus and the server unit is executed by the first certification processing means provided at the collation charging apparatus and the second certification processing means provided at the server unit thereafter to give the second communication address to the collation processing apparatus, thereby making it possible to prevent unfair or illegal access based on "impersonation" by a third party.

The invention claimed is:

1. A collation processing apparatus attached to an external equipment having a network connecting function, the collation processing apparatus comprising:
 bio-information input means for inputting bio-information of a user;
 user bio-information memory means for storing regular user bio-information serving as bio-information of a regular user registered in advance;
 collating means for collating the bio-information input by the bio-information input means with the regular user bio-information stored in the regular user bio-information memory means;
 communication address memory means for storing a communication address serving as identification information which univocally determines the regular user on a network to which the external equipment is connected;
 communication address reading means for reading out a communication address of a collated regular user from the communication address memory means on the basis of a collation result by the collating means;
 communication address output means for outputting the communication address which has been read out by the reading means to the external equipment;
 address setting means for setting the communication address output by the communication address output means in the external equipment;
 user identification information memory means for storing user identification information which identifies the regular user;
 user identification information reading means for reading out predetermined user identification information from the user identification information memory means on the basis of a collation result by the collating means;
 user identification information output means for outputting, to the external equipment, the user identification information which has been read out by the user identification information reading means;
 first communication address receiving means for receiving a first communication address transmitted from a dynamic address assigning unit which dynamically assigns an address in accordance with the fact that the external equipment which has acquired the user identification information output by the user identification information output means makes a request for acquisition of a first communication address with respect to the dynamic address assigning unit connected to the network; and
 electronic signature generating means for generating an electronic signature on the basis of the first communication address received at the first communication address receiving means;
 wherein the communication address output means outputs the first communication address and the electronic signature to the external equipment;
 wherein the collation processing apparatus is a removable memory card and the bio-information input means is located on said removable memory card.

2. The collation processing apparatus as set forth in claim 1, further comprising:
 second communication address receiving means for receiving, through the external equipment, a second communication address transmitted in accordance with the fact that the electronic signature has been certified from the server unit existing on the network to the external equipment connected to the network,
 wherein the address setting means sets the second communication address received at the second communication address receiving means to a communication address on the network of the external equipment.

3. The collation processing apparatus as set forth in claim 2, further comprising:
 certifying means for certifying the server unit on the network by electronic signature.

4. A data communication system, comprising:
 a network;
 an information processing unit connected to the network;
 a collation processing unit attached to the information processing unit; and
 a server unit connected to the network,
 wherein the collation processing unit is a removable memory card comprising bio-information input means located on said removable memory card for inputting bio-information of a user, regular user bio-information memory means for storing regular user bio-information serving as bio-information of a regular user registered in advance, collating means for collating bio-information input by the bio-information input means with regular user bio-information stored in the regular user bio-information memory means, user identification information memory means for storing user identification information which identifies the regular user, user identification information reading means for reading out predetermined user identification information from the user identification information memory means on the basis of a collation result by the collating means, user identification information output means for outputting, to the information processing unit, the user identification information which has been read out by the user identification information reading means, address acquiring means for acquiring a first communication address on the basis of the user identification information, electronic signature generating means for generating an electronic signature on the basis of the first communication address acquired at the address acquiring means, electronic signature attached address output means for outputting, to the information processing unit, the electronic signature generated at the electronic signature generating means in the state where the electronic signature is attached to the first communication address, second communication address receiving means for receiving a second communication address transmitted through the network and the information processing unit from the server unit, and address setting means for setting the second communication address received at the second communication address receiving means at the information processing unit, wherein the information processing unit comprises user identification information input means for inputting the user identification information output by the user identification information output means of the collation processing unit, electronic signature attached address input means for inputting the first communication address and the electronic signature which have been output from the electronic signature attached address output means of the collation processing unit, and electronic signature attached address transmitting means for transmitting, through the network to the server unit, the first communication address and the electronic signature which have been input by the electronic signature attached address input means, and wherein the server unit comprises second communication address memory means for storing a second communication address, electronic signature attached address receiving means for receiving the first communication address and the electronic signature which have been transmitted through the network by the electronic signature attached address transmitting means of the information processing unit, certifying means for certifying the electronic signature attached to the first communication address received at the electronic signature attached address receiving means, reading means for reading out the second communication address from the second communication address memory means in accordance with the fact that the electronic signature has been certified by the electronic signature certifying means, and second communication address transmitting means for transmitting the second communication address which has been read out by the reading means to the collation processing unit attached to the information processing unit through the network;

wherein the address acquiring means of the collation processing unit acquires the first communication address transmitted through the information processing unit from a dynamic address assigning unit which is connected to the network and dynamically assigns addresses, and wherein the information processing unit comprises first communication address acquiring means which responds to the fact that user identification information has been input by the user identification information input means to make a request for acquisition of the first communication address to the dynamic address assigning unit connected to the network.

5. The data communication system as set forth in claim 4, wherein user identification information stored in the user identification memory means of the collation processing unit includes a first communication address, and wherein the address acquiring means of the collation processing unit acquires the first communication address from the user identification information memory means.

6. The data communication system as set forth in claim 4, wherein the collation processing unit comprises first certification processing means for certifying the server unit on the network by an electronic signature, and wherein the server unit comprises second certification processing means which certifies the collation processing unit attached to the information processing unit on the network by an electronic signature.

7. The data communication system as set forth in claim 4, wherein the server unit comprises charging means responsive to the fact that the second communication address is transmitted by the second communication address transmitting means so that data communication is started to carry out charging with respect to a user corresponding to the user identification information which has been read out from the user identification information memory means by the user identification information reading means of the collation processing unit attached to the information processing unit.

8. A data communication method for a data communication system in which an information processing unit to which a collation processing unit is attached and a server unit are connected through a network, the data communication method comprising:

allowing the collation processing unit to input bio-information of a user; wherein the collation processing unit is a removable memory card and the bio-information is input via a bio-information input device located on said removable memory card;

allowing the collation processing unit to collate the input bio-information with regular user bio-information of a regular user registered in advance which is stored in regular user bio-information memory means;

allowing the collation processing unit to read out user identification information which identifies the user which is stored in user identification information memory means;

allowing the collation processing unit to output the user identification information which has been read out to the information processing unit;

allowing the information processing unit to input the user identification information output by the collation processing unit;

allowing the collation processing unit to acquire a first communication address on the basis of the user identification information;

allowing the collation processing unit to generate an electronic signature of the acquired first communication address;

allowing the collation processing unit to output the generated electronic signature to the information processing unit in the state where the generated electronic signature is attached to the first communication address;

allowing the information processing unit to input the first communication address and the electronic signature which have been output from the collation processing unit;

allowing the information processing unit to transmit the first communication address and the electronic signature which have been input to the server unit through the network;

allowing the server unit to receive the first communication address and the electronic signature which have been transmitted from the information processing unit through the network;

allowing the server unit to certify the electronic signature attached to the received first communication address;

allowing the server unit to read out a second communication address stored in second communication address memory means in accordance with the fact that the electronic signature has been certified;

allowing the server unit to transmit the second communication address which has been read out to the collation processing unit attached to the information processing unit through the network;

allowing the collation processing unit to receive the second communication address which has been transmitted through the network and the information processing unit from the server unit; and allowing the collation processing unit to set the received second communication address in the information processing unit;

wherein the information processing unit responds to the fact that the user identification information has been input to make a request for acquisition of the first communication address to a dynamic address assigning unit connected to the network and dynamically assigns the address, and wherein the collation processing unit acquires the first communication address transmitted from the dynamic address assigning unit through the information processing unit.

9. The data communication method as set forth in claim 8, wherein the user identification information includes the first communication address, and wherein the collation unit acquires the first communication address from the user identification information memory means.

10. The data communication method as set forth in claim 8, wherein after the electronic signature has been certified at the server unit, the collation processing unit certifies the server unit on the network by the electronic signature, the server unit certifies the collation processing unit attached to the information processing unit on the network by the electronic signature, and the server unit responds to the fact that the collation processing unit and the server unit have been caused to undergo mutual certification to read out the second communication address stored in the second communication address memory means.

11. The data communication method as set forth in claim 8, wherein the server unit responds to the fact that the second communication address is transmitted so that data communication is started to carry out charging with respect to the user corresponding to the user identification information which has been read out from the user identification information memory means of the collation processing unit attached to the information processing unit.

* * * * *